United States Patent
Pinczewski et al.

Patent Number: 6,123,710
Date of Patent: *Sep. 26, 2000

[54] PROCESS AND ARTICLE FOR KNEE RECONSTRUCTION

[75] Inventors: Leo A. Pinczewski; Gregory J. Roger, both of New South Wales, Australia

[73] Assignee: Smith & Nephew, Inc., Andover, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/630,352

[22] Filed: Apr. 11, 1996

[30] Foreign Application Priority Data

Apr. 12, 1995 [AU] Australia ................. PN2387

[51] Int. Cl.⁷ ................................. A61B 17/58
[52] U.S. Cl. .......................... 606/73; 606/72
[58] Field of Search ................. 606/65, 72, 73, 606/60, 66, 86, 88; 411/244, 389

[56] References Cited

U.S. PATENT DOCUMENTS

| | | |
|---|---|---|
| 1,453,921 | 5/1923 | Cline ........................ 411/244 |
| 2,242,003 | 5/1941 | Lorenzo . |
| 2,267,925 | 12/1941 | Johnston . |
| 4,463,753 | 8/1984 | Gustilo . |
| 4,537,185 | 8/1985 | Stednitz . |

(List continued on next page.)

FOREIGN PATENT DOCUMENTS

| | | |
|---|---|---|
| 14615/28 | 7/1928 | Australia . |
| 59999/90 | 2/1991 | Australia . |
| 0172130 | 2/1986 | European Pat. Off. . |
| 0241792 | 10/1987 | European Pat. Off. . |
| 0260970 | 3/1988 | European Pat. Off. . |
| 0282789 | 9/1988 | European Pat. Off. . |
| 0317406 | 5/1989 | European Pat. Off. . |
| 0374088 | 6/1990 | European Pat. Off. . |
| 451932A1 | 4/1991 | European Pat. Off. . |
| 2622790 | 5/1989 | France . |
| 8916764 | 6/1991 | France . |
| 2 663 837 | 1/1992 | France . |
| 2687911 | 9/1993 | France . |
| 2688689 | 9/1993 | France . |
| 2704140A3 | 10/1994 | France . |
| 2529669 | 3/1976 | Germany . |
| 2747312 | 4/1979 | Germany . |
| 2818254 | 10/1979 | Germany . |
| 4127550 | 2/1993 | Germany . |
| 5300917 | 11/1993 | Japan . |
| 1600752 A1 | 10/1990 | U.S.S.R. . |
| WO89/09030 | 10/1989 | WIPO . |
| WO90/08510 | 8/1990 | WIPO . |
| WO92/03980 | 3/1992 | WIPO . |

OTHER PUBLICATIONS

European Patent Abstracts, Week 9240, p. 235, EP 506420–A1.

(List continued on next page.)

*Primary Examiner*—Michael Buiz
*Assistant Examiner*—Julian W. Woo
*Attorney, Agent, or Firm*—Fish & Richardson P.C.

[57] ABSTRACT

The invention comprises a method of reconstructing the anterior cruciate ligament in the right knee of a patient comprising the steps of forming a tendon graft of tendon, other soft tissue, ligament (including bone blocks if required), or artificial tendon; forming a hole into or through the lateral condyle of the patient's right femur from a point in the intercondylar notch therein, the hole extending anteriorly and laterally; forming a suitably positioned hole through the patient's right tibia opening at one end adjacent the medial tibial spine of the tibia; drawing one end of the tendon graft into the hole in the femur and simultaneously or sequentially drawing the other end of the tendon graft into the hole in the tibia; inserting the leading end of a suitable screw having a left handed thread into the hole in the femur from the intercondylar notch until the trailing end of the screw is at least adjacent he surface of the intercondylar notch; and after tensioning the tendon graft appropriately, securing the other end of the tendon graft to the tibia. A suitable screw for securing a tendon graft is also disclosed.

11 Claims, 1 Drawing Sheet

U.S. PATENT DOCUMENTS

| | | |
|---|---|---|
| 4,744,793 | 5/1988 | Parr et al. . |
| 4,772,286 | 9/1988 | Goble et al. . |
| 4,775,380 | 10/1988 | Seedhom et al. . |
| 4,828,562 | 5/1989 | Kenna . |
| 4,870,957 | 10/1989 | Goble et al. . |
| 4,927,421 | 5/1990 | Goble et al. . |
| 4,950,270 | 8/1990 | Bowman et al. . |
| 4,988,351 | 1/1991 | Paulos et al. . |
| 5,084,050 | 1/1992 | Draenert . |
| 5,116,337 | 5/1992 | Johnson . |
| 5,129,902 | 7/1992 | Goble et al. . |
| 5,129,906 | 7/1992 | Ross et al. . |
| 5,139,520 | 8/1992 | Rosenberg . |
| 5,209,753 | 5/1993 | Biedermann et al. ............... 606/72 |
| 5,211,647 | 5/1993 | Schmieding . |
| 5,246,441 | 9/1993 | Ross et al. .......................... 606/72 |
| 5,281,422 | 1/1994 | Badylak et al. . |
| 5,285,040 | 2/1994 | Brandberg et al. . |
| 5,383,878 | 1/1995 | Roger et al. . |
| 5,443,468 | 8/1995 | Johnson . |
| 5,443,509 | 8/1995 | Boucher et al. ..................... 606/65 |
| 5,454,811 | 10/1995 | Huebner . |
| 5,456,685 | 10/1995 | Huebner . |
| 5,470,334 | 11/1995 | Ross et al. .......................... 606/72 |
| 5,628,766 | 5/1997 | Johnson ............................... 606/73 |
| 5,632,748 | 5/1997 | Beck et al. . |
| 5,674,224 | 10/1997 | Howell et al. . |

OTHER PUBLICATIONS

European Patent Abstracts, Week 9240, p. 189, EP 506213–A1.

European Patent Abstracts, Week 9237, p. 161, EP 502698–A1.

European Patent Abstracts, Week 9212, p. 267, EP 475–889–A.

European Patent Abstracts, Week 9208, p. 99, EP 471–419–A.

European Patent Abstracts, Week 9206, p. 99, EP 469–441–A.

European Patent Abstracts, Week 9144, p. 250, EP 454–601–A.

European Patent Abstracts, Week 9143, p. 28, EP 452–442–A.

European Patent Abstracts, Week 9106, p. 29, EP 411–109–A.

European Patent Abstracts, Week 9118, p. 74, EP 424–734–A.

European Patent Abstracts, Week 9133, p. 77, EP 440–991–A.

European Patent Abstracts, Week 9133, EP 441–065–A.

European Patent Abstracts, Week 9134, p. 177, EP 442–629–A.

Kurosaka M. et al., Am Journal of Sports Med., vol. 15, No. 3, pp. 225–229, "A Biochemical Comparison of Different Surgical Techniques of Graft Fixation in Anterior Cruciate Ligament Reconstruction."

Lambert K.L., Clinical Orthopedics and Related Research, No. 72, Jan./Feb. 1983, pp. 85–89, "Vascularized Patella Tendon Graft with Rigid internal Fixation for Anterior Cruciate Ligament Insufficiency."

PROCESS AND ARTICLE FOR KNEE RECONSTRUCTION

FIELD OF THE INVENTION

The present invention relates to an improved process for knee reconstruction and in particular to an improved process for the replacement of an anterior cruciate ligament in the knee.

BACKGROUND ART

As is well known the human knee comprises an articulation of the femur, the tibia and the patella. The femur and the tibia are maintained in a condition of stable articulation by a number of ligaments of which the principal ones are the anterior and posterior cruciate ligaments and the lateral ligaments. The rupture of the anterior cruciate ligament is relatively commonly encountered as a result of sporting injury or the like. This rupture leads to knee instability and can be a debilitating injury.

There have been a number of procedures designed to reconstruct the anterior cruciate ligament. Initially, attempts were made to replace the anterior cruciate ligament with tendons harvested from elsewhere in the body. These tendons were connected respectively to the femur and the tibia by staples, screws or the like inserted exteriorly into the bone and forming an external attachment to which the tendon could be connected externally of the bone. In some cases, the tendon passed over the top of one of the femoral condyles before attachment to the femur and in other cases a hole was drilled through the femur from outside the bone into the intercondylar notch. These attempts at anterior cruciate ligament reconstruction had mixed success. The tendon tended to break at its point of connection to the bone, or become loose over time, indicating that the tendon bone interface was crucial for effective anterior cruciate ligament reconstruction.

These problems led to the use of bone-tendon-bone grafts generally harvested from mid-third patella tendon with a bone block at each end. Each bone block is inserted into an appropriate hole drilled in the femur or the tibia and secured in place by a screw driven between the wall of the hole and the bone block. While this system has been very successful in many respects a significant number of patients continue to have patella-femoral problems, especially over the mid-third patella tendon donor sites.

In an effort to overcome these problems it has been proposed to suture hamstring tendon to a bone block derived from coring the tibial tunnel and to thereby manufacture a bone/tendon/bone graft similar to a mid-third patella tendon graft. The present inventors have found that the bone quality is extremely variable. This results in poor fixation and poor intra-operative pull-out strength in some cases. This procedure was also found to be a very demanding surgical procedure, and therefore difficult to reproduce.

In all of these operations a hole is drilled into the femur in the region of the intercondylar notch to receive the replacement ligament. In order to ensure that the femoral end of the ligament is correctly placed the hole must be drilled laterally of the mid-line of the femoral notch and in a direction which is angled away from that mid-line. The hole itself extends anteriorly and laterally of the intercondylar notch. This means that, when looking from in front of a patient, the hole for a replacement ligament in the right knee extends into or through the left hand condyle and the hole for a replacement ligament in the left knee extends into or through the right hand condyle.

The present inventors have found that a conventional screw works acceptably in the left hand knee but not so well in the right hand knee. In the case of the right hand knee the present inventors have found that the ligament replacement, which should form a crescent at the back, ie. the posterior side, of the hole, tends to rotate in the hole moving forwardly as it is moved around the hole by the motion of the screw being driven into the hole. This rotation of the ligament has two deleterious consequences. Firstly, the movement of the ligament obscures the surgeons view of the head of the screw. This complicates the operation and means it is more likely that the screw will not be driven fully into the hole as is required for a successful operation. Secondly, the positioning of the ligament may not be correct leading to an increased likelihood of subsequent knee instability.

DISCLOSURE OF THE INVENTION

The present invention consists in a method for the reconstruction of the anterior cruciate ligament in the right knee of a patient comprising the steps of:

(a) forming a tendon graft of tendon, other soft tissue, ligament (including bone blocks if required), or artificial tendon;

(b) forming a hole into or through the lateral condyle of the patient's right femur from a point in the intercondylar notch therein, the hole extending anteriorly and laterally;

(c) forming a suitably positioned hole through the patient's right tibia opening at one end adjacent the medial tibial spine of the tibia;

(d) drawing one end of the tendon graft into the hole in the femur and simultaneously or sequentially drawing the other end of the tendon graft into the hole in the tibia;

(e) inserting the leading end of a suitable screw having a left handed thread into the hole in the femur from the intercondylar notch until the trailing end of the screw is at least adjacent the surface of the intercondylar notch; and (f) after tensioning the tendon graft appropriately, securing the other end of the tendon graft to the tibia.

In another aspect the invention consists in the improvement in an anterior cruciate ligament reconstruction operation in a patient's right knee, comprising using a screw having a left handed thread to secure a tendon graft in a laterally directed hole in the lateral condyle of the femur of the knee which hole opens into the intercondylar notch.

In a still further aspect the present invention consists in a surgical screw having a shank with a longitudinal axis, a thread extending along a length of the shank from one end of the shank, the thread being devoid of an outer cutting line along at least a part of its length, a head at an opposite end of the shank, the head having an outer surface extending smoothly and continuously from an adjacent part of the shank, the outer surface including a hemispherical end portion having a diameter at least equal to a maximum diameter of the said part of the shank and a recess in the head for an insertion tool, the screw being characterised in that the thread is left handed.

It is preferable that the part of the thread of the screw which will come into firm contact with the tendon graft has a soft thread.

It is believed by the present invention that due to the slight tension the tendon graft during insertion of the screw the tendon graft will not be moved by the screw in such a way as to lengthen the graft. It is postulated that using a right handed screw in the left knee does not give rise to unwanted rotation of the tendon graft as such rotation would tend to lengthen the graft. While this explanation is not binding on the present invention it does seem to explain why advantages have been found in using a screw having a left handed thread when carrying out similar operations in the right knee. It is conceivable that another reason for the phenomenon is that the bone at the rear of the hole is denser than that in front. This latter reason has not been verified and is advanced to show that there may be a number of factors contributing to the effect.

The screw may be of any suitable type however it is preferred that the screw has the other activities of U.S. Pat. No. 5,383,878 ie. a rounded head, a soft thread and cannulation. The operation is preferably carried out as is described in a U.S. patent application filed on Jan. 24, 1995 in the names of Gregory James Roger and Leo Arieh Pinczweski the contents whereof are incorporated herein by reference.

BRIEF DESCRIPTION OF THE DRAWINGS

Hereinafter given by way of example only is a preferred embodiment of the present invention described with reference to the accompanying drawings in which.

BEST MODE OF CARRYING OUT THE INVENTION

Figure 1:
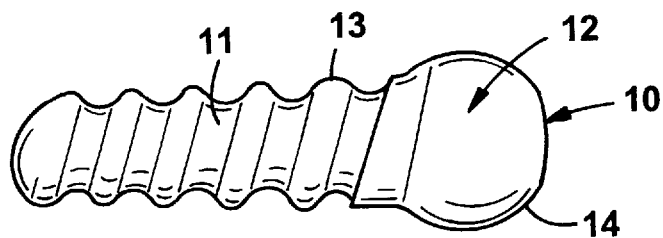
FIG. 1 is a perspective view of a screw for use in the present inventionl
Figure 2:
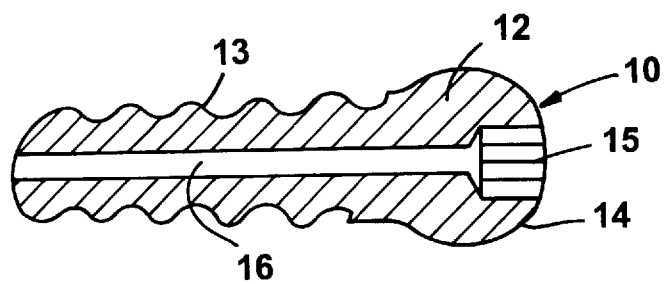
FIG. 2 is a longitudinal cross-sectional view through the screw of FIG. 1.
Figure 3:
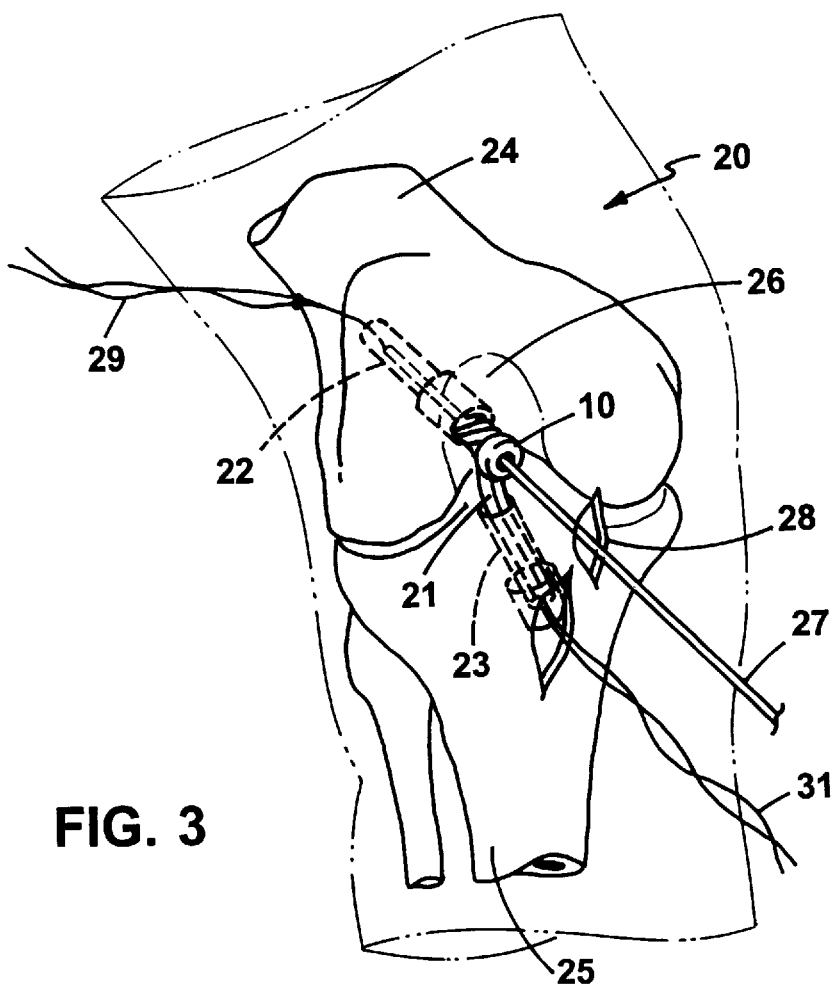
FIG. 3 is a schematic perspective view showing the placement of a screw to secure a tendon graft in a hole in the lateral condyle of a patient's right knee.

The screw 10 shown in FIGS. 1 and 2 is particularly suitable for carrying out the anterior cruciate ligament reconstruction according to the present invention. The screw 10 comprises a shank 11 and a head 12. The shank 11 is formed along its length from its free end distal to the head 12 with a left handed thread 13. The thread 13 is sinusoidal in longitudinal section, that is, it has no outermost cutting line that would normally helically follow the thread crest.

The head 12 has a surface which extends smoothly and continuously from the shank 11 into a hemispherical section 14. Central of the head 12 and aligned with the axis of the screw 10 is a hexagonal socket 15 for accepting a mating hexagonal drive to screw the screw 10 into position. In order to more easily guide and align the screw 10 as it is first inserted into a hole, a central cannulation 16 is present along the longitudinal axis of the screw 10 from the socket 15 to the free end of the shank 11.

In carrying out the operation according to the invention the patient's right knee 20 is prepared in the usual manner and routing arthroscopy performed prior to the operation.

A tendon graft 21 is harvested in the normal manner. This may be a combination o the semitendonosus and gracilis tendons from the patient or it may be bone-tendon-bone graft harvested, for instance, from mid-third patella tendon with a bone block at each end.

Once the tendon graft 21 has been harvested suitable holes 22 and 23 are drilled in the femur 24 and the tibia 25 to receive the tendon graft 2 in known manner. The femoral hole 22 is drilled from a point 30° from the top of the notch (the 11 o'clock position) and 5 mm from the back of the intercondylar notch 26 on a lateral wall thereof. A guide hole is drilled approximately 20° anteriorly and 30° laterally with respect to the femur. A beath pin is then placed through the hole and a cannulated awl or drill is used to enlarge the hole 22 to a size suitable to receive the tendon graft 21.

After the tendon graft 21 has been drawn into the hole 22, and the hole 23 is desired, it is secured in place using the screw 10.

In preparation for placing the screw 10 a guide wire 27 is introduced through an anteriormedial portal 25 and the tip placed at the femoral hole 22 entrance, between the edge of the hole and the tendon graft 21. The knee is then fully flexed and the guide wire run up into the tunnel between the graft 21 and the femoral hole 22 wall.

Once the surgeon is satisfied that the graft 21 and the wire 27 are correctly placed, by direct vision, a screw 10 and a driver (not shown) are run over the wire 27 and into the joint. The tendon 21 is positioned at the back of the hole 22 with the screw anterior to it. Once the tip of the screw 10 is engaged between the graft 21 and the bone surface a firm tap with a mallet to encourage thread grip and to bed the graft down into the hole may be used. While this is done threads 29 and 31 attached to respective ends of the tendon graft 21 are kept taut minimising the tendency for the screw to wind up the graft 21.

The screw 10 is left handed threaded meaning that it must be screwed into the hole 22 in an anti-clockwise fashion. If the movement of screw 10 is to cause the tendon graft 21 to rotate within the hole 22 it will cause the tension in the thread 31 and the tendon graft 21 to increase. This is to be contrasted with the situation in which a conventional right handed threaded screw is used in which the tendon graft 31 could rotate forwardly slackening the tension in the tendon graft 21. It will be appreciated that if the tendon graft 21, which will assume a crescent shape as it is pressed against the side wall of the hole 22 by the screw 10, were to rotate forwardly in the hole it would cover the head 12 of the screw 10 and prevent or impair direct visualisation of the head 12 during completion of the insertion process.

After insertion of the screw 10 in the femoral hole 22 the anterior cruciate ligament reconstruction is completed in a conventional manner by the internal or external affixiation of the other end of the tendon graft, under appropriate tension, to the patient's tibia. The usual routine procedures to testing, irrigation, drainage and closure then follow.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A surgical screw comprising an elongate shank having a first end and a second end, the shank having a length, a threadless, rounded head adjacent to and extending beyond said second end and configured to engage an insertion tool, and a thread extending along at least a part of the length of said shank from said first end, wherein said thread is a left-handed thread and is devoid of an outer cutting line along at least a part of its length, and wherein the surgical screw is configured for the reconstruction of the anterior cruciate ligament in the right knee of a patient by inserting a first end of a graft into a hole in the patient's right femur and inserting the screw into the hole in the femur to secure the graft.

2. The surgical screw of claim 1, wherein the head includes an outer surface extending smoothly and continuously from the shank.

3. The surgical screw of claim 2, wherein the outer surface includes a hemispherical end portion having a diameter at least equal to a maximum diameter of the shank.

4. The surgical screw of claim 3, wherein the diameter of the hemispherical end portion is greater than the maximum diameter of the shank.

5. The surgical screw of claim 1, wherein engaging the insertion tool comprises receiving the tool.

6. The surgical screw of claim 1, wherein the shank is cannulated from the first end to an outer surface of the head.

7. A surgical screw comprising:

a cannulated, elongate shank having a first end and a second end;

a threadless, rounded head adjacent to and extending beyond the second end and configured to engage an insertion tool, wherein the cannulation passes from the first end to an outer surface of the head; and a left-handed thread extending along at least a part of the length of the shank from the first end.

8. A surgical screw comprising a cannulated, elongate shank having a first end and a second end, the shank having a length, a threadless, rounded head adjacent to and extending beyond the second end and configured to engage an insertion tool, the cannulation passing from the first end to an outer surface of the head, and a thread extending along at least a part of the length of the shank from the first end, wherein the thread is a left-handed thread and is devoid of an outer cutting line along at least a part of its length, wherein the surgical screw is configured for securing a tendon graft in reconstruction of the right knee by inserting a first end of a graft into a hole in a femur and inserting the screw into the hole in the femur to secure the graft.

9. The surgical screw of claim 8, wherein the outer surface extends smoothly and continuously from the shank.

10. The surgical screw of claim 9, wherein the outer surface includes a hemispherical end portion having a diameter at least equal to a maximum diameter of the shank.

11. The surgical screw of claim 10, wherein the diameter of the hemispherical end portion is greater than the maximum diameter of the shank.

\* \* \* \* \*